(12) United States Patent
Hoekstra et al.

(10) Patent No.: US 6,765,004 B1
(45) Date of Patent: Jul. 20, 2004

(54) INDOLOAZEPINES AS VASOPRESSIN RECEPTOR ANTAGONISTS

(75) Inventors: William J. Hoekstra, Chapel Hill, NC (US); Michael N. Greco, Lansdale, PA (US); Leonard R. Hecker, Harleysville, PA (US); Bruce E. Maryanoff, Forest Grove, PA (US); Jay M. Matthews, Lansdale, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/592,520

(22) Filed: Jun. 12, 2000

Related U.S. Application Data

(60) Provisional application No. 60/139,628, filed on Jun. 17, 1999.

(51) Int. Cl.[7] .......................... A61K 31/55; A61P 9/12; C07D 487/06
(52) U.S. Cl. ....................... 514/215; 540/577
(58) Field of Search ........................... 514/215; 540/577

(56) References Cited

FOREIGN PATENT DOCUMENTS

| DE | 35 25 564 A1 | 2/1987 |
|---|---|---|
| EP | 0 620 216 A1 | 10/1994 |
| EP | 0 709 386 | 5/1996 |
| WO | WO 87/00522 | 1/1987 |

OTHER PUBLICATIONS

Comepensatory Mechanism associated with congestive heart failure as targets for drug treatment, P.A.von Zweiten, Progress in Pharmacology and Clinical Pharmacology Vol 7/3 pp 49–66 (1990).

Orally Active, Nonpeptide Vasopressin V2 Receptor Antagonists: A Novel Series of 1–[4–A(Benzoylamino) benzoyl] –2,3,4,5–tetrahydro–1H–benzazepines and Related Compounds, Hidenori Ogawa, et al, Journal of Medicinal Chemistry Vol 39, No 18 pp. 3547–3555 (1996).

Orally Active, Nonpeptide Vasopressin V2 Receptor Antagonists: A Novel Series if 1–[4–A(Benzoylamino) benzoyl] –2,3,4,5–tetrahydro–1H–benzazepines and Related Compounds, Hidenori Ogawa, et al, Journal of Medicinal Chemistry Vol 39, No 18 pp. 3547–3555 (1996).

A Synthesis of 1,3,4,5–Tetrahydropyrrolo [4,3,2–de] quinoline, J. B. Hester, Jr., J. Org. Chem., Vol 29. p. 1158, (1964).

Azepinoindoles III. 3,4,5,6–Tetrahydro–1H–azepino [4,3, 2–cd] indoles, J. B. Hester, Jr., J. Org. Chem., Vol 32, pp. 4095–4098 (1967).

PCT Search Report for (ORT–1247) PCT/US00/16549, 2000.

*Primary Examiner*—Brenda Coleman

(57) ABSTRACT

The invention is directed to tricyclic indoloazepine compounds useful as vasopressin receptor antagonists, pharmaceutical compositions comprising the compounds of the present invention and methods of treating conditions involving increased vascular resistance and cardiac insufficiency which include hypertension, congestive heart failure, cardiac insufficiency, coronary vasospasm, cardiac ischemia, liver cirrhosis, renal vasospasm, renal failure, cerebral edema and ischemia, stroke, thrombosis or water retention in a subject in need thereof.

16 Claims, No Drawings

INDOLOAZEPINES AS VASOPRESSIN RECEPTOR ANTAGONISTS

This application claims benefit of and priority from U. S. provisional patent application 60/139,628 filed June 17, 1999.

FIELD OF THE INVENTION

This invention relates to novel tricyclic vasopressin receptor antagonists. By interrupting the binding of the peptide hormone vasopressin to its receptors, the antagonists are useful for treating conditions involving increased vascular resistance and cardiac insufficiency.

BACKGROUND OF THE INVENTION

Vasopressin is a nonapeptide hormone that is secreted primarily from the posterior pituitary gland. The hormone effects its actions through the vascular V-1 and renal V-2 receptor subtypes. The functions of vasopressin include contraction of uterine, bladder and smooth muscle; stimulation of glycogen breakdown in the liver; release of corticotropin from the anterior pituitary; induction of platelet aggregation; and central nervous system modulation of behaviors and stress responses. The V-1 receptor mediates the contraction of smooth muscle and hepatic glycogenolytic and central nervous system effects of vasopressin. The V-2 receptor, presumably found only in the kidney, effects the antidiuretic actions of vasopressin via stimulation of adenylate cyclase.

Elevated plasma vasopressin levels appear to play a role in the pathogenesis of congestive heart failure (P. A. Van Zwieten, *Progr. Pharmacol. Clin. Pharmacol.* 1990, 7, 49). As progress toward the treatment of congestive heart failure, nonpeptide vasopressin V-2 receptor antagonists have induced low osmolality aquaresis and decreased peripheral resistance in conscious dogs with congestive heart failure (H. Ogawa, *J. Med. Chem.* 1996, 39, 3547). In certain pathological states, plasma vasopressin levels may be inappropriately elevated for a given osmolality, thereby resulting in renal water retention and hyponatremia. Hyponatremia, associated with edematous conditions (cirrhosis, congestive heart failure, renal failure), can be accompanied by the syndrome of inappropriate secretion of antidiuretic hormone (SIADH). Treatment of SIADH-compromised rats with a vasopressin V-2 antagonist has corrected their existing hyponatremia (G. Fujisawa, *Kidney Int.* 1993, 44(1), 19). Due in part to the contractile actions of vasopressin at its V-1 receptor in the vasculature, vasopressin V-1 antagonists have reduced blood pressure as a potential treatment for hypertension as well.

Thus, vasopressin receptor antagonists are useful as therapeutics for treating a condition selected from hypertension, congestive heart failure, cardiac insufficiency, coronary vasospasm, cardiac ischemia, liver cirrhosis, renal vasospasm, renal failure, cerebral edema and ischemia, stroke, thrombosis or water retention in a subject in need thereof.

SUMMARY OF THE INVENTION

The present invention is directed to compounds represented by the following general formula (I):

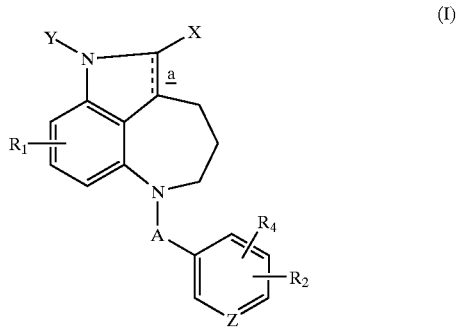

wherein:
A is selected from C(O), $SO_2$ or $CH_2$; preferably, A is C(O);
a represents a single or double bond;
X is selected from hydrogen, halogen, acyl, $C_1$–$C_{10}$ alkyl, ar$C_1$–$C_{10}$ alkyl, $C_1$–$C_{10}$ alkylsulfonyl, arylsulfonyl, $C_1$–$C_{10}$ alkylamino$C_1$–$C_6$ alkyl, $SO_3H$ or =O when a is a single bond; preferably, X is hydrogen, $SO_3H$, or =O;
Y is selected from hydrogen, $C_1$–$C_6$ alkyl, ar$C_1$–$C_6$ alkyl, $C_1$–$C_6$ alkylcarbonyl, $C_1$–$C_6$ alkoxycarbonyl, arylcarbonyl, $C_1$–$C_6$ alkylsulfonyl, arylsulfonyl, $C_1$–$C_6$ alkylaminocarbonyl; preferably, Y is hydrogen;
Z is selected from N or CH;
$R_1$ is selected from hydrogen, $C_1$–$C_{10}$ alkyl, $C_1$–$C_{10}$ alkoxy, halogen, amino $C_1$–$C_{10}$ alkyl or nitro;
$R_2$ is selected from hydrogen, $NR_3COAr$, $NR_3CO$-heteroaryl, $NR_3Ar$, CH=CH—Ar, CF=CH—Ar, CH=CF—Ar, CCl=CH—Ar, CH=CCl—Ar, CH=CH-heteroaryl, CF=CH-heteroaryl, CH=CF-heteroaryl, —CCl=CH-heteroaryl, CH=CCl-heteroaryl, $OCH_2$—Ar, $OCH_2$-heteroaryl or $NR_3CH_2Ar$; wherein the Ar group may be unsubstituted or substituted with one to three substituents independently selected from $C_1$–$C_{10}$ alkyl, $C_1$–$C_{10}$ alkoxy, fluorinated $C_1$–$C_{10}$ alkyl, fluorinated $C_1$–$C_{10}$ alkoxy, halogen, cyano, hydroxy, amino, nitro, $C_1$–$C_{10}$ alkylamino, or unsubstituted, mono-, di- or tri-substituted phenyl, wherein the substituents on the phenyl are independently selected from $C_1$–$C_{10}$ alkyl, $C_1$–$C_{10}$ alkoxy, fluorinated $C_1$–$C_{10}$ alkyl, fluorinated $C_1$–$C_{10}$ alkoxy, halogen, cyano, hydroxy, amino, nitro, $C_1$–$C_{10}$ alkylamino, or heteroaryl; and wherein the heteroaryl group may be unsubstituted or substituted with one to three substituents independently selected from $C_1$–$C_{10}$ alkyl, halogen, aryl, heteroaryl, $C_1$–$C_{10}$ alkoxy, $C_1$–$C_{10}$ alkylamino, arylamino, nitro or hydroxy; preferably, $R_2$ is $NR_3COAr$; more preferably, $R_2$ is NHCOAr wherein the Ar group is phenyl substituted with unsubstituted, mono-substituted or di-substituted phenyl wherein the substituents on the phenyl are independently selected from $C_1$–$C_4$ alkyl, $C_1$–$C_4$ alkoxy, fluorinated $C_1$–$C_4$ alkyl, fluorinated $C_1$–$C_4$ alkoxy, halogen, cyano, hydroxy, amino, nitro, $C_1$–$C_4$ alkylamino, or heteroaryl; most preferably, $R_2$ is NHCOAr wherein the Ar group is substituted phenyl wherein the substituent on the phenyl is selected from phenyl or tolyl;

$R_3$ is selected from hydrogen or $C_1-C_{10}$ alkyl; preferably, $R_3$ is hydrogen or methyl; more preferably, $R_3$ is hydrogen; and, $R_4$ is selected from hydrogen, $C_1-C_{10}$ alkyl, $C_1-C_{10}$ alkoxy, halogen, fluorinated $C_1-C_{10}$ alkyl (e.g., trifluoromethyl) or fluorinated $C_1-C_{10}$ alkoxy (e.g., trifluoromethoxy);

and pharmaceutically acceptable salts thereof.

Exemplifying the invention is the compound of formula (I) selected from:

6-[4-[[(4'-Methyl-2-biphenyl-)carbonyl]amino]benzoyl]-3,4,5,6-tetrahydro-1H-azepino[4,3,2-cd]indole;

6-[4-[[(2-Methyl-3-furanyl)carbonyl]amino]benzoyl]-3,4,5,6-tetrahydro-1H-azepino[4,3,2-cd]indole;

6-[4-[[(4'-Methyl-2-biphenyl-)carbonyl]amino]benzoyl]-1-methyl-3,4,5,6-tetrahydro-1H-azepino[4,3,2-cd]indole;

6-[4-[[(4'-Methyl-2-biphenyl-)carbonyl]amino]benzoyl]-1-acetyl-3,4,5,6-tetrahydro-1H-azepino[4,3,2-cd]indole;

6-[4-[[(2-Biphenyl-)carbonyl]amino]benzoyl]-3,4,5,6-tetrahydro-1H-azepino[4,3,2-cd]indole;

6-[4-[[(2-Biphenyl-)carbonyl]amino]benzoyl]-3,4,5,6-tetrahydro-1H-azepino[4,3,2-cd]-2-indolone;

6-[4-[[(2-Biphenyl-)carbonyl]amino]benzoyl]-2-chloro-3,4,5,6-tetrahydro-1H-azepino[4,3,2-cd]indole;

6-[4-[[(2-Biphenyl-)carbonyl)amino]benzoyl]-2-(N,N-dimethylaminomethyl)-3,4,5,6-tetrahydro-1H-azepino[4,3,2-cd]indole;

6-[4-[[(2-Biphenyl-)carbonyl]amino]benzoyl]-3,4,5,6-tetrahydro-1H-azepino[4,3,2-cd]indole-2-sulfonic acid; or, 6-[4-[[(2-Biphenyl-)carbonyl]amino]2-chlorobenzoyl]-3,4,5,6-tetrahydro-1H-azepino[4,3,2-cd]indole-2-sulfonic acid;

and pharmaceutically acceptable salts thereof.

Illustrative of the invention is a pharmaceutical composition comprising a pharmaceutically acceptable carrier and any of the compounds described above. Illustrating the invention is a pharmaceutical composition made by mixing any of the compounds described above and a pharmaceutically acceptable carrier. An illustration of the invention is a process for making a pharmaceutical composition comprising mixing any of the compounds described above and a pharmaceutically acceptable carrier.

Exemplifying the invention is a method of treating a condition mediated by a vasopressin receptor in a subject in need thereof comprising administering to the subject a therapeutically effective amount of any of the compounds or pharmaceutical compositions described above.

An example of the invention is a method of treating a condition selected from hypertension, congestive heart failure, cardiac insufficiency, coronary vasospasm, cardiac ischemia, liver cirrhosis, renal vasospasm, renal failure, cerebral edema and ischemia, stroke, thrombosis or water retention (preferably, congestive heart failure) in a subject in need thereof comprising administering to the subject a therapeutically effective amount of any of the compounds or pharmaceutical compositions described above.

Further exemplifying the invention is the method of treating the condition (preferably, congestive heart failure), wherein the therapeutically effective amount of the compound is from about 0.1 mg/kg/day to about 300 mg/kg/day.

Also included in the invention is the use of any of the compounds described above for the preparation of a medicament for treating a condition mediated by a vasopressin receptor in a subject in need thereof. Examples of conditions mediated by a vasopressin receptor include, but are not limited to, hypertension, congestive heart failure, cardiac insufficiency, coronary vasospasm, cardiac ischemia, liver cirrhosis, renal vasospasm, renal failure, cerebral edema and ischemia, stroke, thrombosis or water retention.

DETAILED DESCRIPTION OF THE INVENTION

The present invention provides indoloazepine compounds of the formula (I) useful as antagonists of vasopressin. More particularly, the compounds inhibit the binding of vasopressin to V-1 and V-2 receptors and are, therefore, useful for treating conditions which include, but are not limited to, hypertension, congestive heart failure, cardiac insufficiency, coronary vasospasm, cardiac ischemia, liver cirrhosis, renal vasospasm, renal failure, cerebral edema and ischemia, stroke, thrombosis or water retention.

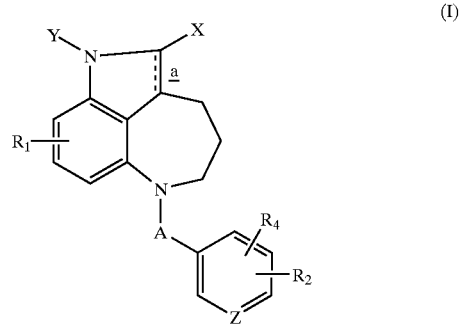

(I)

The indoloazepine compounds of the present invention are vasopressin receptor antagonists. As demonstrated by the results of the pharmacological studies described hereinafter, the compounds of the invention block vasopressin binding to recombinant V-1 and V-2 and decrease arginine vasopressin-elevated blood pressure in animal models.

The compounds of the present invention may also be present in the form of pharmaceutically acceptable salts. For use in medicine, the salts of the compounds of this invention refer to non-toxic "pharmaceutically acceptable salts." Other salts may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benezenesulfonic, oxalic, palmoic, 2-naphthalenesulfonic, p-toluenesulfonic, cyclohexanesulfamic, salicylic, saccharinic and trifluoroacetic acid.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or with common organic solvents, and such solvates are also intended to be encompassed within the scope of this invention.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, unless otherwise noted, the terms "alkyl" and "alkoxy," whether used alone or as part of a substituent group, include straight and branched chains having 1 to 10 carbon atoms or any number within this range. For example, alkyl radicals include methyl, ethyl, n-propyl, isopropyl, n-butyl, isobutyl, sec-butyl, t-butyl, n-pentyl, 3-(2-methyl) butyl, 2-pentyl, 2-methylbutyl, neopentyl, n-hexyl, 2-hexyl and 2-methylpentyl. Also, alkoxy radicals are oxygen ethers formed from the previously described straight or branched chain alkyl groups. Cycloalkyl groups may contain 3 to 10 ring carbons and preferably 5 to 7 carbons. Similarly, alkenyl and alkynyl groups include straight and branched chain alkenes and alkynes having 2 to 10 carbon atoms or any number within this range.

The terms "Ar" and "aryl" as used herein are synonymous and refer to an unsubstituted or substituted aromatic group such as phenyl and naphthyl. When the Ar or aryl group is substituted, it may have one to three substituents which are independently selected from $C_1$–$C_{10}$ alkyl, $C_1$–$C_{10}$ alkoxy, fluorinated $C_1$–$C_{10}$ alkyl (e.g., trifluoromethyl), fluorinated $C_1$–$C_{10}$ alkoxy (e.g., trifluoromethoxy), halogen, cyano, hydroxy, amino, nitro, $C_1$–$C_{10}$ alkylamino (i.e., —NH—$C_1$–$C_{10}$ alkyl, —N—[$C_1$–$C_{10}$ alkyl]$_2$), or unsubstituted, mono-, di- or tri-substituted phenyl wherein the substituents on the phenyl are independently selected from $C_1$–$C_{10}$ alkyl, $C_1$–$C_{10}$ alkoxy, fluorinated $C_1$–$C_{10}$ alkyl, fluorinated $C_1$–$C_{10}$ alkoxy, halogen, cyano, hydroxy, amino, nitro, $C_1$–$C_{10}$ alkylamino or heteroaryl.

The term "heteroaryl" as used herein represents a stable unsubstituted or substituted five or six membered monocyclic aromatic ring system or a nine or ten membered benzofused heteroaromatic ring system which consists of carbon atoms and from one to three heteroatoms selected from N, O or S. The heteroaryl group may be attached at any heteroatom or carbon atom which results in the creation of a stable structure. Examples of heteroaryl groups include, but are not limited to pyridinyl, pyrazinyl, pyridazinyl, pyrimidinyl, thiophenyl, furanyl, imidazolyl, isoxazolyl, oxazolyl, pyrazolyl, pyrrolyl, thiazolyl, thiadiazolyl, triazolyl, benzimidazolyl, benzofuranyl, benzothienyl, benzisoxazolyl, benzoxazolyl, benzopyrazolyl, indolyl, benzothiazolyl, benzothiadiazolyl, benzotriazolyl and quinolinyl. Prefered heteroaryl groups include pyridinyl, thiophenyl, furanyl and quinolinyl. When the heteroaryl group is substituted, the heteroaryl group may have one to three substituents which are independently selected from $C_1$–$C_{10}$ alkyl, halogen, aryl, heteroaryl, $C_1$–$C_{10}$ alkoxy, $C_1$–$C_{10}$ alkylamino, arylamino, nitro or hydroxy.

The term "aralkyl" means an alkyl group substituted with an aryl group (e.g., benzyl, phenylethyl). Similarly, the term "aralkoxy" indicates an alkoxy group substituted with an aryl group (e.g., benzyloxy). The term aminoalkyl refers to an alkyl group substituted with an amino group (i.e., alkyl-$NH_2$). The term "alkylamino" refers to an amino group substituted with an alkyl group and includes both monoalkylamino and dialkylamino (i.e., —NH-alkyl, —N—[alkyl]$_2$); in the case of dialkylamino, the alkyl groups can be the same or different.

The term "acyl" as used herein means an organic radical having 2 to 6 carbon atoms (branched or straight chain) derived from an organic acid by removal of the hydroxyl group.

The term "halogen" shall include iodine, bromine, chlorine and fluorine.

Whenever the term "alkyl" or "aryl" or either of their prefix roots appear in a name of a substituent (e.g., aralkyl, alkylamino) it shall be interpreted as including those limitations given above for "alkyl" and "aryl." Designated numbers of carbon atoms (e.g., $C_1$–$C_6$) shall refer independently to the number of carbon atoms in an alkyl or cycloalkyl moiety or to the alkyl portion of a larger substituent in which alkyl appears as its prefix root.

It is intended that the definition of any substituent or variable at a particular location in a molecule be independent of its definitions elsewhere in that molecule, It is understood that substituents and substitution patterns on the compounds of this invention can be selected by one of ordinary skill in the art to provide compounds that are chemically stable and that can be readily synthesized by techniques know in the art as well as those methods set forth herein.

Under standard nomenclature used throughout this disclosure, the terminal portion of the designated side chain is described first, followed by the adjacent functionality toward the point of attachment. Thus, for example, a "phenyl $C_1$–$C_6$ alkylamido $C_1$–$C_6$ alkyl" substituent refers to a group of the formula:

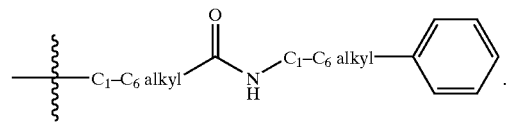

As used herein, the term "composition" is intended to encompass a product comprising the specified ingredients in the specified amounts, as well as any product which results, directly or indirectly, from combinations of the specified ingredients in the specified amounts.

The utility of the compounds to treat disorders of increased vascular resistance and cardiac insufficiency can be determined according to the procedures described herein. The present invention therefore provides a method of treating disorders of increased vascular resistance and cardiac insufficiency in a subject in need thereof which comprises administering any of the compounds or pharmaceutical compositions as defined herein in a quantity effective to treat such thrombotic disorders. The compound may be administered to a patient by any conventional route of administration, including, but not limited to, intravenous, oral, subcutaneous, intramuscular, intradermal and parenteral.

The present invention also provides pharmaceutical compositions comprising one or more compounds of this invention in association with a pharmaceutically acceptable carrier.

To prepare the pharmaceutical compositions of this invention, one or more compounds of formula (I) or salt thereof of the invention as the active ingredient, is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, easpoonful and the like, from about 0.03 mg/kg to about 100 mg/kg (preferred from about 0.1 mg/kg to about 30 mg/kg) and may be given at a dosage of from about 0.1 mg/kg/day to about 300 mg/kg/day (preferred from about 1 mg/kg/day to about 50 mg/kg/day). The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums and other pharmaceutical diluents, e.g. water, to form a solid preformulation composition containing a homogeneous mixture of a compound of the present invention or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided Into unit dosage forms of the type described above containing from about 0.1 mg to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known in the art.

The method of treating vascular resistance disorders described in the present invention may also be carried out using a pharmaceutical composition comprising any of the compounds as defined herein and a pharmaceutically acceptable carrier. The pharmaceutical composition may contain from about 0.01 mg to about 100 mg of the compound (preferably from about 5 mg to about 50 mg) and may be constituted into any form suitable for the mode of administration selected. Carriers include necessary and inert pharmaceutical excipients, including, but not limited to, binders, suspending agents, lubricants, flavourants, sweeteners, preservatives, dyes and coatings. Compositions suitable for oral administration include solid forms, such as pills, tablets, caplets, capsules (each including immediate release, timed release and sustained release formulations), granules, powders and liquid forms, such as solutions, syrups, elixirs, emulsions and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavoured suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine and phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol or polyethyl eneoxide-polylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyeric acid, polyorthoesters, polyacetals, polydihydropyrans, polycyanoacrylates and cross-linked and amphipathic block copolymers of hydrogels.

Compounds of this invention may be administered in any of the foregoing compositions and according to dosage regimens established in the art whenever treatment of thrombotic disorders is required.

The daily dosage of the products may be varied over a wide range from about 0.01 mg to about 1,000 mg per adult human per day. For oral administration, the compositions are preferably provided in the form of tablets containing about 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 100 mg/kg of body weight per day. Preferably, the range is from about 0.03 mg/kg to about 10 mg/kg of body weight per day. The compounds may be administered on a dosage regimen of about once per day to about 4 times per day.

Optimal dosages to be administered may be readily determined by those skilled in the art, and will vary with the particular compound used, the mode of administration, the strength of the preparation, the mode of administration and the advancement of the disease condition. In addition, factors associated with the particular patient being treated, including patient age, weight, diet and time of administration will result in the need to adjust dosages.

Abbreviations used in the instant specification, particularly the Schemes and Examples, are as follows:

| | |
|---|---|
| DCM | Dichloromethane |
| DMF | N,N-Dimethylformamide |
| $Et_2O$ | Diethyl ether |
| EtOAc | Ethyl acetate |
| EtOH | Ethanol |
| h | hour |
| HPLC | High Performance Liquid Chromatography |
| LAH | Lithium aluminum hydride |
| Me | Methyl |
| MeOH | Methanol |
| min | Minutes |
| NaH | Sodium hydride |
| NCS | N-chlorosuccinimide |
| NT | Not tested |
| Ph | Phenyl |
| rt | Room temperature |
| THF | Tetrahydrofuran |
| TFA | Trifluoroacetic acid |
| Tol | Toluene |

Particularly preferred compounds of the present invention include those compounds shown in Table I.

TABLE I

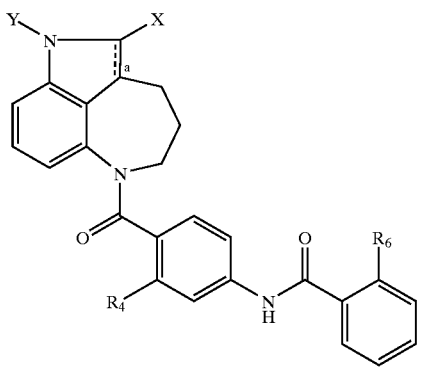

| Cmpd | a | $R_4$ | $R_6$ | X | Y |
|---|---|---|---|---|---|
| 10 | Double bond | H | Ph | H | H |
| 11 | Double bond | H | p-Tol | H | H |
| 12 | See structure below | | | | |
| 13 | Double bond | H | p-Tol | H | Me |
| 14 | Double bond | H | p-Tol | H | Ac |
| 15 | Single bond | H | Ph | =O | H |
| 16 | Double bond | H | Ph | Cl | H |
| 17 | Double bond | H | Ph | $CH_2NMe_2$ | H |
| 18 | Double bond | H | Ph | $SO_3H$ | H |
| 19 | Double bond | Cl | Ph | $SO_3H$ | H |

Compound 12:

TABLE I-continued

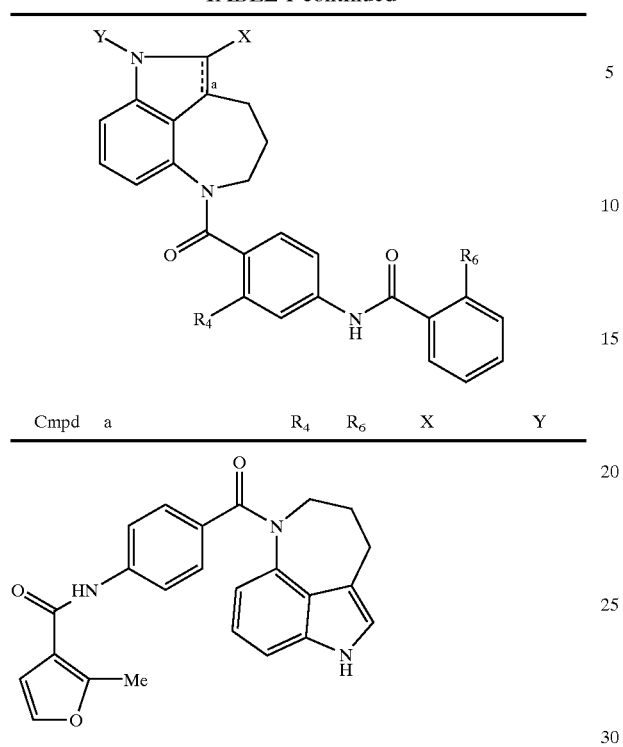

| Cmpd | a | R₄ | R₆ | X | Y |
|------|---|-----|-----|---|---|

Scheme M illustrates a general method of preparing compounds of the invention (for a synthesis of intermediate amine 8, see also J. Hester *J. Org. Chem.* 1967, 32, 4095). 4-Nitroindole and formaldehyde/dimethylamine were condensed to form 4-nitrogramine (2). Compound 2 underwent nucleophilic substitution with diethyl malonate to afford diester 3, which was then reduced to the amine 4 via hydrogenolysis over palladium-on-carbon. Indole 4 was cyclized thermally to lactam 5, and then underwent decarboxylation by treatment with potassium hydroxide followed by heating neat to give unsubstituted lactam 7. The lactam 7 was reduced with LAH to afford amine 8, which was acylated with acid chloride 9 (prepared by acylation of methyl 4-aminobenzoate with 2-biphenylcarbonyl chloride followed by sodium hydroxide-mediated saponification of the ester to the acid, and then thionyl chloride-mediated conversion to the acid chloride 9) to give the final product compound 10.

SCHEME AA

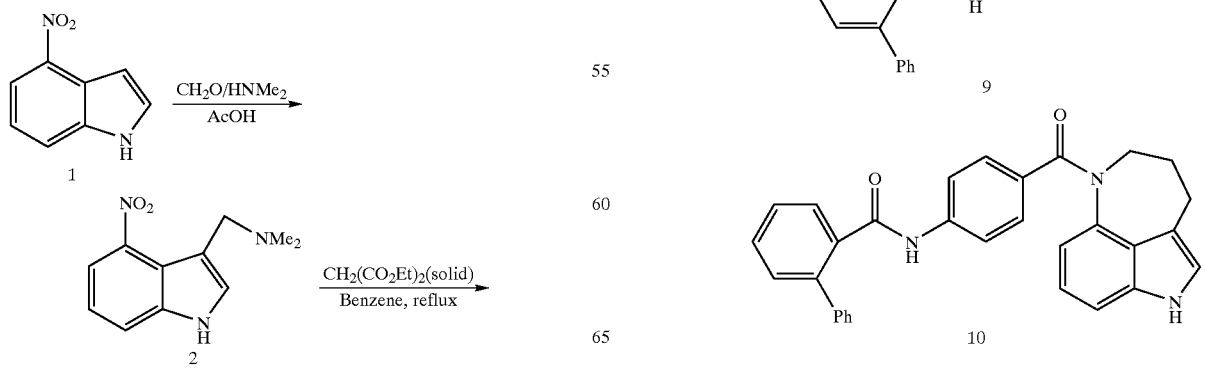

Scheme AB illustrates a general method of preparing N-substituted indole compounds of the invention, exemplified by compounds 13 and 14.

Compound AB1 (prepared by acylation of amine 8 with 4-nitrobenzoyl chloride) was de-protonated with sodium hydride and then reacted with an appropriate electrophile (methyl iodide or acetyl chloride for these examples) to give the N-substituted intermediates. These intermediates were then reduced to the corresponding amines with zinc dust, and acylated with 2-biphenylcarbonyl chloride to give products exemplified by compounds 13 and 14.

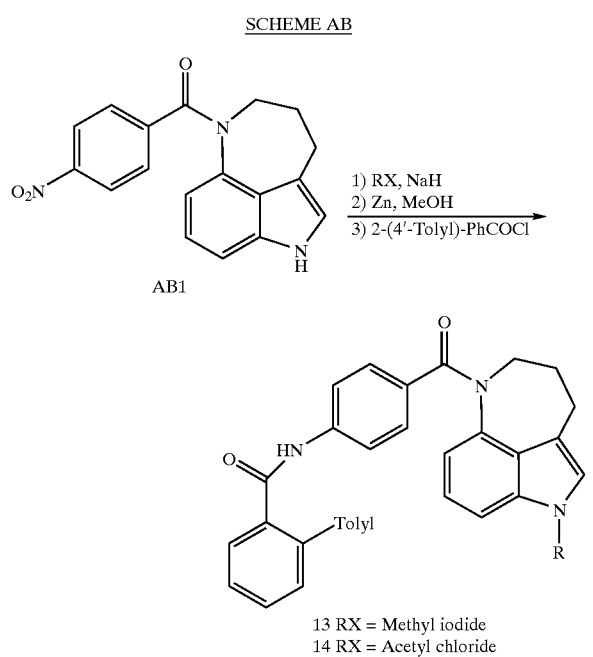

SCHEME AB

1) RX, NaH
2) Zn, MeOH
3) 2-(4'-Tolyl)-PhCOCl

13 RX = Methyl iodide
14 RX = Acetyl chloride

Scheme AC illustrates a general method of preparing two substituted indole compounds of the invention in a single pot, exemplified by compounds 15 and 16. In this procedure, compound 10 was treated with 15 N-chlorosuccinimide at ambient conditions to afford the aforementioned product compounds 15 and 16 upon chromatographic separation.

SCHEME AC

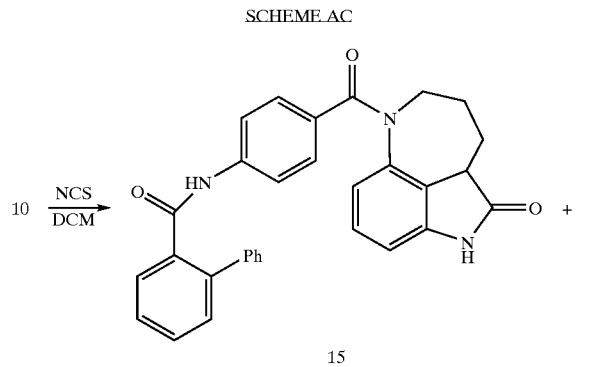

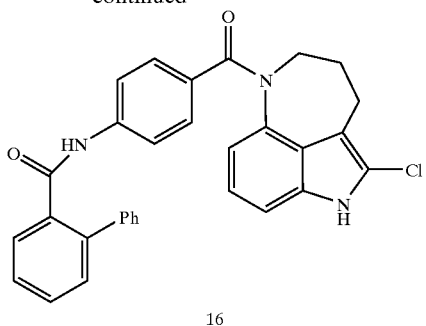

16

Scheme AD illustrates a general method of preparing sulfonic acid compounds of the invention, exemplified by compound 18. Compound 10 was treated with chlorosulfonic acid at ambient conditions to give the aforementioned product compound 18.

SCHEME AD

10 →[ClSO$_3$H / DCM]

18

Reagents were purchased from Aldrich Chemical Company. High field $^1$H NMR spectra were recorded on a Bruker AC-360 spectrometer at 360 MHz, and coupling constants are given in Herz. Melting points were determined on a Mel-Temp II melting point apparatus and are uncorrected. Microanalyses were performed at Robertson Microlit Laboratories, Inc., Madison, N.J. and are expressed in percentage by weight of each element per total molecular weight. In those cases where the product is obtained as a salt, the free base is obtained by methods known to those skilled in the art, e.g. by basic ion exchange purification. Nuclear magnetic resonance (NMR) spectra for hydrogen atoms were measured in the indicated solvent with tetramethylsilane (TMS) as the internal standard on a Bruker AM-360 (360 MHz) spectrometer. The values are expressed in parts per million down field from TMS. The mass spectra (MS) were determined on a Finnigan 3300 spectrometer (methane), using desorption chemical ionization techniques. Unless otherwise noted, the materials used in the examples were obtained from readily available commercial suppliers or synthesized by standard methods known to one skilled in the art of chemical synthesis. The substituent groups, which vary between examples, are hydrogen unless otherwise noted.

EXAMPLE 1

6-[4-[[(2-Biphenyl-)carbonyl]amino]benzoyl]-3,4,5,6-tetrahydro-1H-azepino[4,3,2-cd]indole (10)

Lactam 7 was prepared by the method of J. Hester (*J. Org. Chem.* 1967, 32, 4095) starting from 4-nitrogramine (20 grams). A suspension of 7 (11.2 g, 0.06 mol), LAH (11 g) and THF (1.2 L) under argon was heated at reflux for about 6 h, cooled to about rt, placed in an ice bath and treated with water dropwise (11 mL). This mixture was treated with NaOH (10%, 20 mL), then warmed to about rt and filtered through dicalite with $Et_2O$ washes. The light amber filtrate was concentrated in vacuo to give a dark oil. The oil was dissolved in $Et_2O$:EtOAc (1:1, 100 mL), treated with charcoal, filtered through silica gel and evaporated to give amine 8 as an amber oil (8.9 g). Acid chloride 9, prepared by reflux of the corresponding carboxylic acid (0.67 g, 0.0021 mol) with thionyl chloride (20 mL) followed by repetitive evaporation with $CH_2Cl_2$, was treated sequentially with $CH_2Cl_2$ (20 mL), amine 8 (0.34 g, 0.002 mol) and triethylamine (0.50 g, 0.005 mol) while cooled in an ice bath. The ice bath was removed and the reaction stirred for about 16 h. The reaction was diluted with saturated $NaHCO_3$, and the layers separated. The organic layer was dried ($Na_2SO_4$), evaporated and purified over silica gel (EtOAc/$CHCl_3$ eluent) to give compound 10 as a tan solid. MS m/e 472.56 ($MH^+$). Anal. calcd. for $C_{31}H_{25}N_3O_2 \cdot 0.05$ EtOAc·$0.35CHCl_3 \cdot 0.1H_2O$ (519.55): C, 72.94; H, 5.03; N, 8.09; Cl, 7.16. Found: C, 73.05; H, 5.24; N, 7.84; Cl, 7.39.

EXAMPLE 2

6-[4-[[(4'-Methyl-2-biphenyl-)carbonyl]amino] benzoyl]-3,4,5,6-tetrahydro-1H-azepino[4,3,2-cd] indole (11)

Compound 11 (yellow powder) was prepared as described in Example 1. $^1H$ NMR ($CDCl_3$) 2.2 (t, J=6, 2 H), 2.34 (s, 3 H), 2.7 (m, 1H), 3.1 (t, J=6, 2 H), 4.2 (m, 1H), 6.2 (d, J=7, 1 H), 6.8 (t, J=8, 1 H), 6.9–7.7 (m, 14 H), 7.8 (d, J=7, 1 H), 8.1 (s, 1H). MS m/e 486.58 ($MH^+$).

EXAMPLE 3

6-[4-[[(2-Methyl-3-furanyl)carbonyl]amino] benzoyl]-3,4,5,6-tetrahydro-1H-azepino[4,3,2-cd] indole (12)

Compound 12 (yellow powder) was prepared as described in Example 1. $^1H$ NMR ($CDCl_3$) 2.3 (t, J=4, 2 H), 2.6 (s, 3 H), 3.1 (m, 2 H), 4.1 (m, 2 H), 6.2 (d, J=6, 1 H), 6.7 (m, 2 H), 7.1 (m, 2 H), 7.2 (m, 3 H), 7.4 (d, J=5, 2 H), 8.7 (s, 1H), 9.5 (s, 1H). MS m/e 400.44 ($MH^+$).

EXAMPLE 4

6-[4-[[(4'-Methyl-2-biphenyl-)carbonyl]amino] benzoyl]-1-methyl-3,4,5,6-tetrahydro-1H-azepino[4, 3,2-cd]indole (13)

A solution of AB1 (0.11 g, 0.35 mmol; prepared by acylation of amine 8 with 4-nitrobenzoyl chloride/ triethylamine) in DMF (1.8 mL) was treated with sodium hydride (60%, 0.015 g, 1.3 eq), stirred for about 15 min and treated with methyl iodide (0.028 mL, 1.3 eq). The reaction was stirred for about 15 min, diluted with water (15 mL) and extracted with EtOAc (3×25 mL). The combined organics were dried (magnesium sulfate) and evaporated to a solid. The solid was triturated with hexane (10 mL) and dried. The dried material was reduced with zinc in methanol and then acylated with 4'-tolyl-2-benzoyl chloride (see Example 1) to afford compound 13 (orange solid). $^1H$ NMR ($CDCl_3$) 2.2 (t, J=4, 2 H), 2.3 (s, 3 H), 3.1 (m, 2 H), 3.3 (m, 2 H), 3.7 (s, 3 H), 6.2 (d, J=6, 1 H), 6.8 (t, J=5, 1 H), 6.9–7.1 (m, 4 H), 7.2–7.6 (m, 10 H), 7.8 (d, J=5, 1 H). MS m/e 500.61 ($MH^+$).

EXAMPLE 5

6-[4-[[(4'-Methyl-2-biphenyl-)carbonyl]amino] benzoyl]-1-acetyl-3,4,5,6-tetrahydro-1H-azepino[4, 3,2-cd]indole (14)

A solution of AB1 (0.18 g, 0.56 mmol; prepared by acylation of amine 8 with 4-nitrobenzoyl chloride/ triethylamine) in DMF (2 mL) was treated with sodium hydride (60%, 0.025 g, 1.3 eq), stirred for about 15 min and treated with acetyl chloride (0.052 mL, 1.3 eq). The reaction was stirred for about 2 h, diluted with water (20 mL) and extracted with EtOAc (3×25 mL). The combined organics were dried (magnesium sulfate), evaporated and purified by silica gel chromatography (3:1 hexane:EtOAc) to give a yellow solid. The purified material was reduced with zinc dust in methanol and then acylated with 4'-tolyl-2-benzoyl chloride (see Example 1) to afford compound 14 (yellow solid). $^1H$ NMR ($CDCl_3$) 2.2 (m, 2 H), 2.3 (s, 3 H), 2.6 (s, 3 H), 3.0 (m, 2 H), 4.1 (m, 3 H), 6.4 (d, J=6, 1 H), 7.0 (m, 3 H), 7.1–7.6 (m, 10 H), 7.8 (d, J=5, 1 H), 8.1 (d, J=4, 1 H). MS m/e 528.62 ($MH^+$).

EXAMPLE 6

6-[4-[[(2-Biphenyl-)carbonyl]amino]benzoyl]-3,4,5, 6-tetrahydro-1H-azepino[4,3,2-cd]-2-indolone (15)

A mixture of 10 (0.047 g, 0.1 mmol), N-chlorosuccinimide (0.026 g, 2 eq) and argon de-gassed $CH_2Cl_2$ (40 mL) was stirred under argon for about 18 h and evaporated to a solid. The solid was purified by preparative HPLC (MeCN:water, 1:3) to give two products compound 15 and 16. Compound 15 was afforded as a white powder. Anal. calcd. for $C_{31}H_{25}N_3O_3 \cdot 1.5H_2O$ (514.58): C, 72.36; H, 5.48; N, 8.17. Found: C, 72.13; H, 5.18; N, 8.10. MS m/e488.55 ($MH^+$).

EXAMPLE 7

6-[4-[[(2-Biphenyl-)carbonyl]amino]benzoyl]-2-chloro-3,4,5,6-tetrahydro-1H-azepino[4,3,2-cd] indole (16)

Compound 16 (white powder) was prepared as described in Example 6. $^1H$ NMR (DMSO-$d_6$) 2.1 (m, 2 H), 2.5 (m, 2 H), 3.0 (m, 2 H), 6.1 (d, J=6, 1 H), 6.7 (t, J=6, 1 H), 7.0 (m, 4 H), 7.2–7.7 (m, 10 H), 10.2 (s, 1 H), 11.0 (s, 1 H). MS m/e 506.10 and 508.10 ($MH^+$).

EXAMPLE 8

6-[4-[[(2-Biphenyl-)carbonyl]amino]benzoyl]-2-(N, N-dimethylaminomethyl)-3,4,5,6-tetrahydro-1 H-azepino[4,3,2-cd]indole (17)

A mixture of 10 (0.10 g, 0.2 mmol), N, N-dimethylmethyleneammonium chloride (0.10 g, 5.3 eq) and $CH_2Cl_2$ (25 mL) was stirred under argon for about 2 h and diluted with water (5 mL). The layers were separated and the organic layer was washed with water (5 mL), dried (sodium sulfate) and evaporated to give 17 (clear glass). $^1H$ NMR (DMSO-$d_6$) 2.1 (m, 2 H), 2.22 (s, 6 H), 3.0 (m, 2 H), 3.3 (m, 1 H), 4.0 (m, 1 H), 4.79 (s, 2 H), 6.2 (d, J=7, 1 H), 6.8 (t, J=7, 1 (d, J=8, 2 H), 7.2–7.6 (m, 13 H), 10.31 (s, 1 H). MS m/e 529.65 ($MH^+$).

EXAMPLE 9

6-[4-[[(2-Biphenyl-)carbonyl]amino]benzoyl]-3,4,5, 6-tetrahydro-1H-azepino[4,3,2-cd]indole-2-sulfonic acid (18)

A solution of 10 (0.20 g, 0.42 mmol) in $CH_2Cl_2$ (100 mL) at about 0° C. was treated with chlorosulfonic acid (0.056 g, 1.1 eq) and stirred for about 2 h. The reaction was warmed to about rt, stirred for about 18 h and evaporated to a tan powder. The powder was purified by preparative HPLC (MeCN:water, 1:3) to give 18 (tan powder). $^1$H NMR (DMSO-$d_6$) 2.1 (m, 4 H), 3.0 (m, 1 H), 3.2 (t, J=4, 1 H), 6.1 (m, 1 H), 6.7 (t, J=6, 1 H), 6.9 (d, J=5, 1 H), 7.1 (m, 4 H), 7.3–7.6 (m, 9 H), 10.3 (br. s, 2 H), 11.1 (s, 1 H). MS m/e 552.62 (MH$^+$).

EXAMPLE 10

6-[4-[[(2-Biphenyl-)carbonyl]amino]2-chlorobenzoyl]-3,4,5,6-tetrahydro-1 H-azepino (4,3,2-cd]indole-2-sulfonic acid (19)

Compound 19 was prepared as described in Example 9 and isolated as a light tan powder. $^1$H NMR (DMSO-$d_6$) 2.1 (m, 4 H), 3.0 (m, 1 H), 3.2 (t, J=4, 1 H), 6.1 (m, 1 H), 6.7 (t, J=6, 1 H), 6.9 (d, J=5, 1 H), 7.1 (m, 4 H), 7.3–7.6 (m, 8 H), 10.3 (br. s, 2 H), 11.1 (s, 1 H). MS m/e 586.19 and 588.19 (MH$^+$).

EXAMPLE 11

As a specific embodiment of an oral composition, about 100 mg of compound 10 of Example 1 is formulated with sufficient finely divided lactose to provide a total amount of from about 580 mg to about 590 mg to fill a size O hard gel capsule.

EXAMPLE 12
In Vitro Recombinant Vasopressin Receptor Binding Assay

Compounds were assessed for their ability to displace $^3$H-arginine vasopressin from the human V-1 or V-2 receptor in HEK-293 cells. Assay buffer is 50 mM Tris-Cl, 5 mM MgCl$_2$, 0.1% BSA (pH 7.5) containing 5 ug/ml of aprotinin, leupeptin, pepstatin, 50 ug/ml bacitracin, and 1 mM Pefabloc. $^3$H-vasopressin is $^3$H-arginine-8-vasopressin (68.5Ci/mmol, final concentration in assay is from 0.65nM to 0.75nM). Into wells of 96-well round bottom polypropylene plates were added buffer, test compound, membrane (containing cloned human V-1 or V-2 receptor), and $^3$H-vasopressin. The reaction plates were allowed to sit at rt for 1 h. The samples were filtered through Unifilter GF/C plates presoaked in 0.3 polyethyleneimine). The plates were washed 5 times with cold physiological saline containing 0.05% Tween 20. After drying, the bottom of the filter plates were sealed and 0.025 ml of Microscint-20 was added to each filter. The top of the plate was sealed, and the plate was counted. Non-specific binding was determined by the addition of 1.25 uM arginine-8-vasopressin in those wells.

EXAMPLE 13
Reversal of Vasopressin-Induced Hypertension in Rats

The anti-hypertensive activity of compounds was screened in an anesthetized model of vasopressin-induced hypertension. Male Long Evans, normotensive rats of between 350 and 450 g in body weight were anesthetized with pentobarbital (35 mg/kg, ip) and maintained throughout the procedure with an ip infusion of 10 mg/kg/hr. Arginine vasopressin was infused at 30 ng/kg/min, iv, to induce a stable hypertensive state (ca. 50 mmHg increase in mean arterial blood pressure). Compounds of interest were administered in an ascending dose fashion and the maximum decrease in mean arterial blood pressure was recorded. An ED$_{50}$ was determined from the linear portion of the dose-response relationship for each animal.

This model was modified slightly to assess the bioavailability of compounds of interest. Rather than dosing the animals iv in an ascending dose fashion, a single dose per animal was administered directly into the duodenum. The anti-hypertensive effects were then monitored for 60 min and the maximum percent reversal was calculated.

TABLE II

In Vitro Results

| Cmpd | V1 Bdg (%, 1 M) | V2 Bdg IC$_{50}$ M | V2 cAMP IC$_{50}$ M |
|---|---|---|---|
| 10 | 26% | 0.015 | 0.070 |
| 11 | 33% | 0.011 | 0.069 |
| 12 | 65% | 24% (1.0 M) | NT |
| 13 | 49% | 0.21 | NT |
| 14 | 1% | 0.18 | NT |
| 15 | 39% | 0.011 | 0.64 |
| 16 | 18% | 0.044 | 2.3 |
| 17 | 6% (0.1 M) | >1 | NT |
| 18 | 0% (0.1 M) | 0.013 | NT |
| 19 | 4% (0.1 M) | 0.012 | NT |

TABLE III

In Vivo Blood Pressure Reduction Results

| Cmpd | ID Dose (mg/kg) | BP Reduction (%) |
|---|---|---|
| 10 | 10 | 17% |
| 15 | 10 | 23% |
| 18 | 10 | 13% |
| 19 | 10 | 23% |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of the formula (I):

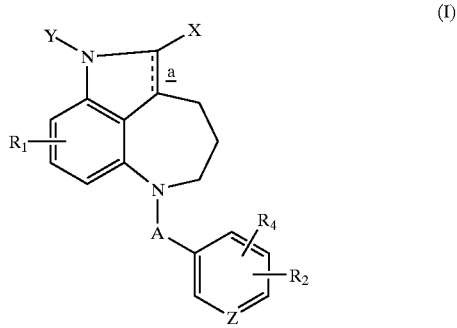

wherein:
  A is selected from C(O), SO$_2$ or CH$_2$;
  a represents a single or double bond;
  X is selected from hydrogen, halogen, acyl, C$_1$–C$_{10}$ alkyl, arylC$_1$–C$_{10}$alkyl, C$_1$–C$_{10}$ alkylsulfonyl, arylsulfonyl, C$_1$–C$_{10}$ alkylaminoC$_1$–C$_6$ alkyl, SO$_3$H, or =O when a is a single bond;
  Y is selected from hydrogen, C$_1$–C$_6$ alkyl, C$_1$–C$_6$ alkylcarbonyl C$_1$–C$_6$ alkoxycarbonyl, arylcarbonyl, C$_1$–C$_6$ alkylsulfonyl, arylsulfonyl, or C$_1$–C$_6$ alkylaminocarbonyl;
  Z is selected from N or CH;
  R$_1$ is selected from hydrogen, C$_1$–C$_{10}$ alkyl, C$_1$–C$_{10}$ alkoxy, halogen, amino C$_1$–C$_{10}$ alkyl or nitro;

19

R$_2$ is selected from hydrogen, —NR$_3$COAr, —NR$_3$CO-heteroaryl, —NR$_3$Ar, —CH=CH—Ar, —CF=CH—Ar, —CH=CF—Ar, —CCl=CH—Ar, —CH=CCl—Ar, —CH=CH-heteroaryl, —CF=CH-heteroaryl, —CH=CF-heteroaryl, —CCl=CH-heteroaryl, —CH=CCl-heteroaryl, —OCH$_2$—Ar, —OCH$_2$-heteroaryl or —NR$_3$CH$_2$Ar; wherein the Ar group may be unsubstituted or substituted with one to three substituents independently selected from C$_1$–C$_{10}$ alkyl, C$_1$–C$_{10}$ alkoxy, fluorinated C$_1$–C$_{10}$ alkyl, fluorinated C$_1$–C$_{10}$ alkoxy, halogen, cyano, hydroxy, amino, nitro, C$_1$–C$_{10}$ alkylamino, or unsubstituted, mono-, di- or tri-substituted phenyl wherein the substituents on the phenyl are independently selected from C$_1$–C$_{10}$ alkyl, C$_1$–C$_{10}$ alkoxy, fluorinated C$_1$–C$_{10}$ alkyl, fluorinated C$_1$–C$_{10}$ alkoxy, halogen, cyano, hydroxy, amino, nitro, C$_1$–C$_{10}$ alkylamino, or heteroaryl; and wherein the heteroaryl group may be unsubstituted or substituted with one to three substituents independently selected from C$_1$–C$_{10}$ alkyl, halogen, aryl, heteroaryl, C$_1$–C$_{10}$ alkoxy, C$_1$–C$_{10}$ alkylamino, arylamino, nitro or hydroxy;

R$_3$ is selected from hydrogen or C$_1$–C$_{10}$ alkyl; and,

R$_4$ is selected from hydrogen, C$_1$–C$_{10}$ alkyl, C$_1$–C$_{10}$ alkoxy, halogen, fluorinated C$_1$–C$_{10}$ alkyl or fluorinated C$_1$–C$_{10}$ alkoxy;

and pharmaceutically acceptable salts thereof.

2. The compound of claim 1, wherein: X is selected from hydrogen, halogen, acyl, C$_1$–C$_6$ alkyl, arylC$_1$–C$_{10}$alkyl, C$_1$–C$_6$ alkylsulfonyl, arylsulfonyl, C$_1$–C$_6$ alkylaminoC$_1$–C$_4$ alkyl, SO$_3$H, or=O when a is a single bond;

Y is selected from hydrogen, C$_1$–C$_3$ alkyl, C$_1$–C$_3$ alkylcarbonyl, C$_1$–C$_3$ alkoxycarbonyl, arylcarbonyl, C$_1$–C$_3$ alkylsulfonyl, arylsulfonyl, or C$_1$–C$_3$ alkylaminocarbonyl;

R$_1$ is selected from hydrogen, C$_1$–C$_6$ alkyl, C$_1$–C$_6$ alkoxy, halogen, aminoC$_1$–C$_6$ alkyl or nitro;

R$_2$ is selected from —NR$_3$COAr, —NR$_3$CO-heteroaryl, —NR$_3$Ar, —CH=CH—Ar, —CF=CH—Ar, —CH=CF—Ar, —CCl=CH—Ar, —CH=CCl—Ar, —CH=CH-heteroaryl, —CF=CH-heteroaryl, —CH=CF—heteroaryl, —CCl=CH—heteroaryl, —CH=CCl—heteroaryl, —OCH$_2$—Ar, —OCH$_2$-heteroaryl or —NR$_3$CH$_2$Ar; wherein the Ar group may be unsubstituted or substituted with one to three substituents independently selected from C$_1$–C$_6$ alkyl, C$_1$–C$_6$ alkoxy, fluorinated C$_1$–C$_6$ alkyl, fluorinated C$_1$–C$_6$ alkoxy, halogen, cyano, hydroxy, amino, nitro, C$_1$–C$_4$ alkylamino, or unsubstituted, mono-, di- or tri-substituted phenyl wherein the substituents on the phenyl are independently selected from C$_1$–C$_6$ alkyl, C$_1$–C$_6$ alkoxy, fluorinated C$_1$–C6 alkyl, fluorinated C$_1$–C$_6$ alkoxy, halogen, cyano, hydroxy, amino, nitro, C$_1$–C$_4$ alkylamino, or heteroaryl; and wherein the heteroaryl group may be unsubstituted or substituted with one to three substituents independently selected from C$_1$–C$_6$ alkyl, halogen, aryl, heteroaryl, C$_1$–C$_6$ alkoxy, C$_1$–C$_4$ alkylamino, arylamino, nitro or hydroxy;

R$_3$ is selected from hydrogen or C$_1$–C$_4$ alkyl; and,

R$_4$ is selected from hydrogen, C$_1$–C$_4$ alkyl, C$_1$–C$_4$ alkoxy, halogen, fluorinated C$_1$–C$_4$ alkyl or fluorinated C$_1$–C$_4$ alkoxy;

and pharmaceutically acceptable salts thereof.

20

3. The compound of claim 2, wherein:

A is C(O);

X is selected from hydrogen, SO$_3$H, or =O;

Y is hydrogen;

R$_2$ is —NR$_3$COAr; and,

R$_3$ is selected from hydrogen or methyl;

and pharmaceutically acceptable salts thereof.

4. The compound of claim 3, wherein:

R$_2$ is —NR$_3$COAr wherein the Ar group is phenyl substituted with unsubstituted, mono-substituted or di-substituted phenyl wherein the substituents on the phenyl are independently selected from C$_1$–C$_4$ alkyl, C$_1$–C$_4$ alkoxy, fluorinated C$_1$–C$_4$ alkyl, fluorinated C$_1$–C$_4$ alkoxy, halogen, cyano, hydroxy, amino, nitro, C$_1$–C$_4$ alkylamino, or heteroaryl;

and pharmaceutically acceptable salts thereof.

5. The compound of claim 4, wherein:

R$_2$ is —NR$_3$COAr wherein the Ar group is substituted phenyl wherein the substituent on the phenyl group is selected from phenyl or tolyl;

and pharmaceutically acceptable salts thereof.

6. The compound of claim 2, selected from:

6-[4-[[(4'-Methyl-2-biphenyl-)carbonyl]amino]benzoyl]-3,4,5,6-tetrahydro-1H-azepino[4,3,2-cd]indole;

6-[4-[[(2-Methyl-3-furanyl)carbonyl]amino]benzoyl]-3,4,5,6-tetrahydro-1H-azepino[4,3,2-cd]indole;

6-[4-[[(4'-Methyl-2-biphenyl-)carbonyl]amino]benzoyl]-1-methyl-3,4,5,6-tetrahydro-1H-azepino[4,3,2-cd]indole;

6-[4-[[(4'-Methyl-2-biphenyl-)carbonyl]amino]benzoyl]-1-acetyl-3,4,5,6-tetrahydro-1H-azepino[4,3,2-cd]indole;

6-[4-[[(2-Biphenyl-)carbonyl]amino]benzoyl]-3,4,5,6-tetrahydro-1H-azepino[4,3,2-cd]indole;

6-[4-[[(2-Biphenyl-)carbonyl]amino]benzoyl]-3,4,5,6-tetrahydro-1H-azepino[4,3,2-cd]-2-indolone;

6-[4-[[(2-Biphenyl-)carbonyl]amino]benzoyl]-2-chloro-3,4,5,6-tetrahydro-1H-azepino[4,3,2-cd]indole;

6-[4-[[(2-Biphenyl-)carbonyl]amino]benzoyl]-2-(N,N-dimethylaminomethyl)-3,4,5,6-tetrahydro-1H-azepino[4,3,2-cd]indole;

6-[4-[[(2-Biphenyl-)carbonyl]amino]benzoyl]-3,4,5,6-tetrahydro-1H-azepino[4,3,2-cd]indole-2-sulfonic acid; or, 6-[4-[[(2-Biphenyl-)carbonyl]amino]2-chlorobenzoyl]-3,4,5,6-tetrahydro-1H-azepino[4,3,2-cd]indole-2-sulfonic acid;

and pharmaceutically acceptable salts thereof.

7. The compound of claim 6, selected from:

6-[4-[[(2-Biphenyl-)carbonyl]amino]benzoyl]-3 ,4,5,6-tetrahydro-1H-azepino[4,3,2-cd]indole;

6-[4-[[(2-Biphenyl-)carbonyl]amino]benzoyl]-3,4,5,6-tetrahydro-1H-azepino[4,3,2-cd]-2-indolone;

6-[4-[[(2-Biphenyl-)carbonyl]amino]benzoyl]-3 ,4,5,6-tetrahydro-1H-azepino[4,3,2-cd]indole-2-sulfonic acid; or, 6-[4-[[(2-Biphenyl-)carbonyl]amino]2-chlorobenzoyl]-3,4,5,6-tetrahydro-1H-azepino[4,3,2-cd]indole-2-sulfonic acid;

and pharmaceutically acceptable salts thereof.

8. A pharmaceutical composition comprising a pharmaceutically acceptable carrier and a compound of claim 1.

9. A pharmaceutical composition made by mixing a compound of claim 1 and a pharmaceutically acceptable carrier.

10. A process for making a pharmaceutical composition comprising mixing a compound of claim 1 and a pharmaceutically acceptable carrier.

11. A method of treating a condition selected from hypertension, congestive heart failure, cardiac insufficiency, coronary vasospasm, cardiac ischemia, liver cirrhosis, renal vasospasm, renal failure, cerebral edema and ischemia, stroke, thrombosis or water retention in a subject in need thereof comprising administering to the subject a therapeutically effective amount of the compound of claim 1.

12. The method of claim 11, wherein the condition is congestive heart failure.

13. The method of claim 11, wherein the therapeutically effective amount of the compound is from about 0.1 mg/kg/day to about 300 mg/kg/day.

14. A method of treating a condition selected from hypertension, congestive heart failure, cardiac insufficiency, coronary vasospasm, cardiac ischemia, liver cirrhosis, renal vasospasm, renal failure, cerebral edema and ischemia, stroke, thrombosis or water retention in a subject in need thereof comprising administering to the subject a therapeutically effective amount of the composition of claim 8.

15. The method of claim 14, wherein the condition is congestive heart failure.

16. The method of claim 14, wherein the therapeutically effective amount of the compound is from about 0.1 mg/kg/day to about 300 mg/kg/day.

\* \* \* \* \*